(12) United States Patent
Weber et al.

(10) Patent No.: US 7,416,645 B2
(45) Date of Patent: Aug. 26, 2008

(54) CONTINUOUS PROCESS FOR RECOVERING ACETONE FROM A WASTE STREAM RESULTING FROM ACETONE PURIFICATION

(75) Inventors: Markus Weber, Haltern (DE); Otto Schnurr, Putte-Kapellen (BE)

(73) Assignee: INEOS Phenol GmbH & Co. KG, Gladbeck (DE)

( * ) Notice: Subject to any disclaimer, the term of this patent is extended or adjusted under 35 U.S.C. 154(b) by 342 days.

(21) Appl. No.: 10/614,680

(22) Filed: Jul. 3, 2003

(65) Prior Publication Data

US 2004/0074758 A1 Apr. 22, 2004

Related U.S. Application Data

(60) Provisional application No. 60/395,868, filed on Jul. 11, 2002.

(51) Int. Cl.
*B01D 3/34* (2006.01)
*C07C 45/78* (2006.01)
*B01D 1/00* (2006.01)

(52) U.S. Cl. ............... 203/29; 203/34; 203/36; 203/78; 203/79; 203/80; 203/99; 203/DIG. 19; 568/383; 568/411

(58) Field of Classification Search ............ 203/78–80, 203/99, DIG. 19, 34, 36, 29; 568/383, 411, 568/749
See application file for complete search history.

(56) References Cited

U.S. PATENT DOCUMENTS

| | | | | |
|---|---|---|---|---|
| 2,351,352 A | | 6/1944 | McAllister et al. | |
| 3,896,006 A | * | 7/1975 | Cooke | 203/28 |
| 4,262,150 A | * | 4/1981 | Pujado | 568/754 |
| 4,298,765 A | * | 11/1981 | Cochran et al. | 203/6 |
| 4,339,605 A | * | 7/1982 | Ligorati et al. | 568/383 |
| 4,340,447 A | * | 7/1982 | Laverick et al. | 203/36 |
| 4,634,796 A | * | 1/1987 | Suciu et al. | 203/6 |
| 4,722,769 A | * | 2/1988 | Chan et al. | 203/30 |
| 6,489,519 B1 | * | 12/2002 | van Barneveld et al. | 568/754 |
| 6,657,087 B2 | * | 12/2003 | Weber et al. | 568/385 |
| 2002/0032350 A1 | * | 3/2002 | Gerlich et al. | 568/383 |
| 2003/0168329 A1 | * | 9/2003 | Fulmer et al. | 203/39 |

FOREIGN PATENT DOCUMENTS

| | | | |
|---|---|---|---|
| EP | 1188737 | | 3/2002 |
| GB | 1 108 327 | * | 4/1968 |
| GB | 1 108 584 | * | 4/1968 |
| GB | 1108327 | | 4/1968 |
| JP | 54070210 A2 | | 6/1979 |
| WO | 94 03420 | * | 2/1994 |

\* cited by examiner

*Primary Examiner*—Virginia Manoharan
(74) *Attorney, Agent, or Firm*—Knobbe, Martens, Olson & Bear LLP

(57) ABSTRACT

The present invention provides a continuous process for recovering acetone from a waste stream from an acetone purification stage. The waste stream contains mesityl oxide and optionally acetone. The process for recovering acetone includes separating the waste stream in a separating device at least in one stream containing mesityl oxide and optionally a further stream containing acetone, then concentrating mesityl oxide in the mesityl oxide containing stream, and finally recycling the concentrated mesityl oxide stream to the separating device and bringing it into contact with a basic or acidic aqueous medium or with an acidic catalyst in the presence of water whereby mesityl oxide is at least partially hydrolyzed to acetone.

21 Claims, 1 Drawing Sheet

# CONTINUOUS PROCESS FOR RECOVERING ACETONE FROM A WASTE STREAM RESULTING FROM ACETONE PURIFICATION

RELATED APPLICATIONS

This application claims the benefit of priority under 35 U.S.C. 119(e) of the U.S. Provisional Patent Application No. 60/395,868, filed Jul. 11, 2002, which is expressly incorporated herein by reference in its entirety.

FIELD OF THE INVENTION

The present invention relates to a continuous process for recovering acetone from a waste stream resulting from an acetone purification stage. In particular, the present invention relates to a process for the manufacture of phenol and acetone from cumene according to the Hock process wherein in one step acetone is recovered in a continuous process from a waste stream of an acetone purification stage by cleavage of mesityl oxide contained therein.

BACKGROUND OF THE INVENTION

It is known from the state of the art that mesityl oxide can be reversed into acetone from which it is formed by treatment under acidic or basic conditions. For example, U.S. Pat. No. 2,351,352 discloses a process for producing isophorone by condensing acetone whereas mesityl oxide which is formed inter alia as a by-product during this reaction is reversed into acetone by commingling the crude product mixture with aqueous sodium hydroxide solution, followed by distilling the thus obtained acetone in one step together with unreacted acetone from the main reaction. This prevents forming further mesityl oxide in case of a preliminary removal of unreacted acetone.

The manufacture of phenol and acetone which is of great economic importance typically proceeds starting from cumene according to the Hock reaction by acid catalyzed cleavage of cumene hydroperoxide. The by-products formed during this reaction, like for example, cumene, benzene and one or more ketones, have to be separated from the main products phenol and acetone, which generally proceeds via extraction and/or distillation.

Often an acetone stream obtained from a preceding distillation to separate it from phenol, is treated with alkaline reagents to further separate it from undesired byproducts, especially aldehydes. Because of these acidic and alkaline reaction conditions, respectively, the acetone partly reacts with itself to form diacetone alcohol in a first step which may either dehydrate to form mesityl oxide or decompose again to redevelop acetone.

Since acetone represents one of the desired products a procedure in which the crude product of the Hock process is directly commingled with an alkaline solution to reverse mesityl oxide contained therein to acetone analogous to U.S. Pat. No. 2,351,352 as mentioned above, is not suitable in this case because under these conditions additional byproducts would be formed which leads to a reduction in yield. Moreover, any further acetone purification steps using an alkaline solution also will result in the production of mesityl oxide which accordingly would not be recovered and therefore as well lead to an additional loss of yield.

Accordingly, EP-A-1 188 737 discloses a process for the work-up of substance streams containing mesityl oxide which are especially obtained from acetone purification during the Hock process.

In this process the mesityl oxide is concentrated and reversed to acetone using an acidic or basic aqueous medium or an acidic catalyst in the presence of water.

The disadvantages of this recovery process for mesityl oxide can be seen in the cleavage taking place in a separate reaction apparatus which increases the costs for new plants to be constructed, as well as the costs for the maintenance of such a plant. Additionally, the only process exemplified therein represents a discontinuous one which is susceptible for disorders.

Abstract of JP-A 79 70,210 also deals with acetone recovery from mesityl oxide in the cumene process of phenol manufacture whereas in this process the alkali required for the conversion is a waste liquor from the acetone purification in the cumene processes. Since the cleavage of mesityl oxide described therein proceeds in an autoclave this process as well requires a separate reaction apparatus.

Accordingly the problem underlying the present invention presents as providing a process for recovering acetone from a waste stream from an acetone purification stage which requires less apparative expenses and preferably reduces maintenance costs as well.

SUMMARY OF THE INVENTION

This problem is inventively solved by providing a continuous process for recovering acetone from a waste stream from an acetone purification stage said waste stream comprising mesityl oxide, and optionally acetone by:
i) separating the waste stream in a separating device at least in one stream comprising mesityl oxide, and optionally in a further stream comprising acetone,
ii) concentrating mesityl oxide in the mesityl oxide containing stream and
iii) recycling the concentrated mesityl oxide stream to the separating device and bringing it into contact with a basic or acidic medium or with an acidic catalyst in the presence of water whereby mesityl oxide is at least partially hydrolyzed to acetone.

A further subject matter of the present invention is a process to manufacture phenol and acetone from cumene according to the Hock process by:
a) oxidizing cumene to form cumene hydroperoxide,
b) subjecting cumene hydroperoxide to acid catalyzed cleavage obtaining a cleavage phase comprising phenol and acetone,
c) separating phenol and acetone,
d) purifying the crude acetone from step C) resulting in a pure acetone product stream and a waste stream, and
e) recovering acetone from the waste stream according to the above-described process.

DETAILED DESCRIPTION OF THE PREFERRED EMBODIMENT

Figure 1:
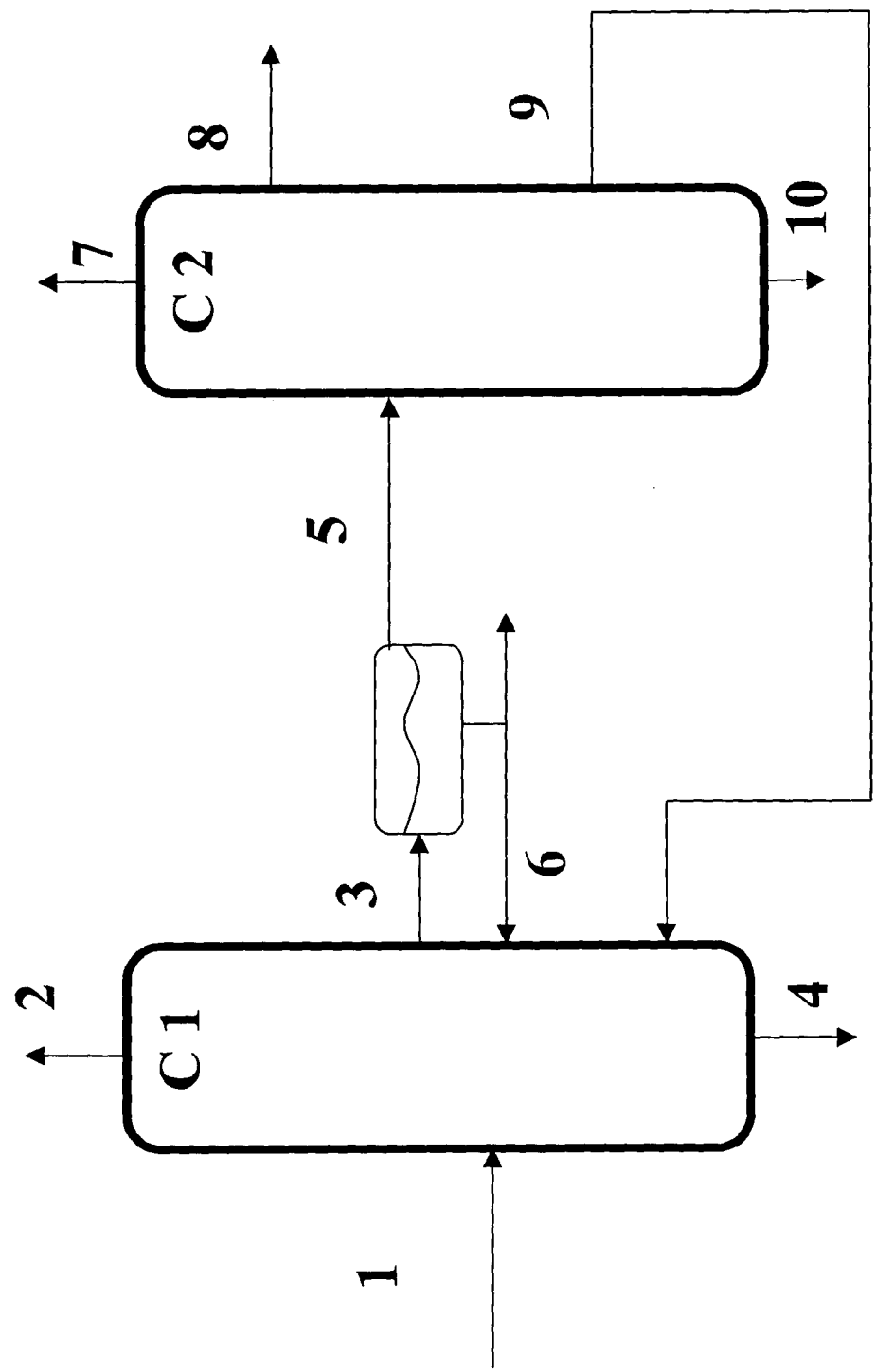
FIG. 1 shows a schematic representation of a preferred embodiment of the present invention.

By developing a continuous process in which the cleavage of the mesityl oxide takes place in the same separating device which is used to separate the mesityl oxide containing, preferably organic, stream from the waste stream, it is possible to reduce the number of reaction columns. This does not only reduce costs when creating a new plant but it also reduces the costs for maintaining the existing plant and therefore being very attractive for industrial purposes. Besides, such a continuous process reduces the manpower required for a smooth processing. Especially the reconduction of the separated purified products into the main process is omitted in the inventive process. In a preferred embodiment a basic aqueous medium which is already present in the waste stream is used to ease the cleavage of mesityl oxide, which leads to further cost reduction and decreases waste disposal.

The mesityl oxide-containing waste stream may be obtained by any kind of acetone purification. Preferably the waste stream results from the acetone purification of crude acetone which is most preferably obtained from the Hock process. Beyond, this waste stream may as well represent a mixture of several side streams obtained during varying purification procedures. The crude acetone may be purified by separating it according to common procedures, for example, in a reaction-distillation column wherein the pure acetone is removed, preferably as a top stream leaving behind the waste stream preferably as a bottom stream.

The inventive process makes use of the reverse of the known reaction in which two molecules of acetone react under basic or acidic conditions in an Aldol reaction to diacetone alcohol which further dehydrates to mesityl oxide. Accordingly, to recover acetone from mesityl oxide-containing waste streams this reaction is reversed which requires bringing the mesityl oxide-containing waste stream into contact with an aqueous medium which may either be basic or acidic or with an acidic catalyst in the presence of water to catalyze the hydration reaction. Such a catalyst is preferably an immobilized heterogeneous catalyst, for example, a zeolite or an acid ion-exchange resin.

As acidic medium, preferably mineral acids or organic acids like hydrochloric acid, sulfuric acid or acidic acid in various concentrations may be used. As basic medium, alkali lyes, like soda lye, or alkaline earth metal lyes as well as organic water containing phases of compounds with basic properties, like amines or phenolates, may be used. Soda lye represents the most preferred basic aqueous medium.

The basic or acidic aqueous medium or the acidic catalyst containing water may be either separately fed to the separating device or be already present in the waste stream. If the aqueous medium is separately fed to the separating device preferably a basic solution containing 1-10wt % sodium hydroxide, more preferably containing 4 wt % sodium hydroxide, is used. It should be further provided that the amount of acidic or basic aqueous medium or acidic catalyst containing water fed to the separating device results in a reaction mixture of waste stream and aqueous medium containing 5-15 percent by volume aqueous medium, based on the total volume of the reaction mixture.

In the preferred embodiment in which the aqueous medium is already present in the waste stream the concentration of the aqueous medium in the waste stream is preferably $\geq 0.1$ percent by volume, more preferably 0.1 to 5 percent by volume, most preferred from 0.1 to 0.2 percent by volume, based on the total volume of the waste stream.

Since at least the recycled mesityl oxide, optionally further components as well, may only be dissolved to a small extent in water, or are not soluble in water at all, to achieve an optimized turnover of the mesityl oxide cleavage reaction it should be provided that the organic and aqueous phases are intensively agitated which may be obtained with common means, preferably making use of pumps, stirrers or a reboiler.

A great advantage of conducting the process wherein a basic aqueous medium is already present in the waste stream, is when the basic aqueous medium is leftover from a preceding acetone purification step; which reduces the amount of basic aqueous medium, especially the solution of sodium hydroxide, required for the whole process, therefore reducing the expense for waste disposal.

Concentration of the mesityl oxide-containing stream may be achieved by common methods, for example, by extraction or distillation, preferably by means of distillation. The concentrated mesityl oxide stream preferably has a mesityl oxide content of more than 20 wt %, more preferred from 30-90 wt %, and most preferred from 50-85 wt %.

In an especially preferred embodiment the process proceeds using a waste stream which contains, in addition to mesityl oxide and optional acetone, one or more organic components having a boiling point higher than acetone which in case that the process represents a part of the work-up stages of the Hock process, for example, may comprise cumene, benzene and/or ketones. In this embodiment a basic medium is chosen as hydrating medium. The recovery of acetone is then achieved by:

a) continuously feeding said waste stream to a middle section of a first distillation column;
b) separating the waste stream in the first distillation column into
   b1) optionally a top stream comprising acetone;
   b2) a side stream comprising mesityl oxide, the organic components and optionally residual acetone; and
   b3) a bottom stream comprising the basic aqueous medium;
c) continuously feeding side stream b2) to a middle section of a second distillation column;
d) separating the side stream b2) in the second distillation column into
   d1) a top stream comprising acetone;
   d2) a side stream comprising mesityl oxide; and
   d3) a bottom stream comprising organic components having a boiling point higher than mesityl oxide; and
e) continuously recycling side stream d2) to the first distillation column to an entry point that is below the removal point for side stream b2).

This process is explained in more detail in combination with the reaction parameters according to FIG. 1.

A waste stream containing mesityl oxide and optionally acetone is continuously fed via line 1 into a middle section of a first distillation column C1 which functions as separating device. The basic aqueous medium preferably containing sodium hydroxide may result from treatment of crude acetone, for example obtained by the Hock process, with aqueous sodium hydroxide solution to remove aldehydes. The separation in the distillation column C1 may proceed with support of common column internals, like reaction trays, hackings and trickle columns, whereas in the preferred embodiment reaction trays are used.

In said first distillation column C1 the waste stream is separated, optionally into a top stream comprising acetone and eventually traces of high boiling hydrocarbons which is removed via line 2, into a side stream comprising mesityl oxide, the organic components and optionally residual acetone removed via line 3 and into a bottom stream comprising the basic aqueous medium partly removed via line 4. The residual acetone removed via line 2 may be transferred back to the separating device from which the used waste stream resulted, which preferably represents the distillation column in which crude acetone from the Hock process is separated into pure acetone and the waste stream. Of course it is as well possible to combine several acetone streams occurring anywhere during the workup procedure of the crude product mixture. The part of the basic aqueous medium contained in the bottom stream which is not required for reversing mesityl oxide to acetone may be transferred to the separating device in which the crude acetone is purified using a basic aqueous medium or be removed, optionally after having been neutralized, as waste water.

According to the preferred embodiment shown in FIG. 1 the side stream removed via line 3 comprising mesityl oxide, the organic components, water and optionally residual acetone is continuously fed to a decanter D, where the aqueous phase and the organic phase are separated. If the distillation column C1 is run in a way that the side stream removed via line 4 does not contain water or only negligible amounts of water the decanter can be omitted. The aqueous phase is at least partially recycled to the distillation column C1 via line 6, or can be discarded as wastewater stream.

The organic phase from decanter D comprising mesityl oxide, the organic components and optionally residual acetone is continuously fed via line 5 to a middle section of a second distillation column C2. The column interiors of said second distillation column may be the same or different from the ones used in the first distillation column C1. In said second distillation column side stream from the first distillation column C1 is separated into a top stream comprising optionally acetone which is removed via line 7, into a side stream comprising mesityl oxide which is removed via line 9 and into a bottom stream comprising organic components having a boiling point higher than mesityl oxide which is removed via line 10.

Analogous to the acetone top stream obtained in the first distillation column the acetone stream of the second distillation column may be further worked up and combined with the pure acetone obtained from any other acetone purification step, preferably it is transferred to the distillation column serving as separating device in which the crude acetone obtained from the Hock process is separated into pure acetone and the waste stream. The mixture of bottom stream components may be either further separated, worked up or transferred to combustion, the resulting energy of which may be used anywhere in the process, for example to heat the distillation columns. Depending on its composition it might be meaningful to transfer the obtained bottom stream to the work-up stage of the final residue of the main reaction.

The side stream removed via line 9 comprising mesityl oxide is continuously recycled to the first distillation column C1 to an entry point that is below the removal point of line 3. In a preferred embodiment in which the first distillation column C1 is equipped with reaction trays the recycled mesityl oxide stream is directed onto one of these reaction trays.

The recycled mesityl oxide is brought into contact with the basic aqueous medium into an area of the first distillation column C1 in which, beside optional residual acetone at least one further organic component can be found which, like mesityl oxide, may only be dissolved to a small extent in water, or which is not soluble in water at all. To achieve an optimized turnover of the mesityl oxide cleavage reaction it should be provided that the organic and aqueous phases are intensively agitated. This agitation may be obtained by common means, preferably making use of pumps, stirrers or a reboiler.

To ease the reaction the cleavage reaction mixture of mesityl oxide and basic aqueous medium, while being agitated should preferably be thermally treated. Accordingly the temperature at the entry point of the recycled mesityl oxide stream should be 30 to 160° C., preferably 70 to 110° C.

In an especially preferred embodiment the second distillation column C2 provides a second side stream that is removed via line 8 comprising ketones and optionally further organic compounds with a boiling point lower than mesityl oxide and higher than acetone, like for example benzene, and which is positioned upwards relative to the position of line 9. It is a particular advantage of the process of the present invention that compounds that are detrimental to the acetone quality, especially benzene, can be easily removed from the process streams without additional separation stages. Said second side stream may be further worked up and separated or transferred to combustion, for example, to use the thus resulting energy for heating the distillation columns.

The bottom stream removed via line 10 from the second distillation column C2 comprises the high boiling hydrocarbons like cumene. Preferably cumene is recovered from said stream and recycled to the cleavage stage of the Hock process. Alternatively the bottom stream may be transferred to combustion to utilize the energy content of said stream.

The process of the present invention can be easily integrated into the Hock process for producing phenol. Thus, a further subject of preferred embodiment of the present invention is a process to manufacture phenol and acetone from cumene according to the Hock process by:
  a) oxidizing cumene to form cumene hydroperoxide,
  b) subjecting cumene hydroperoxide to acid-catalyzed cleavage obtaining a cleavage phase comprising phenol and acetone,
  c) separating phenol and acetone,
  d) purifying the crude acetone from step C) resulting in a pure acetone product stream and a waste stream, and
  e) recovering acetone from a waste stream according to the continuous process described above.

Preferably the crude acetone of step d) is purified using an aqueous sodium hydroxide solution, followed by distillation to obtain a pure acetone product stream and a waste stream whereby the waste stream contains preferably not more than 30% acetone, water, sodium hydroxide, diacetone alcohol, mesityl oxide, cumene, benzene and ketones, and optionally further organic by-products.

In a preferred embodiment said waste stream mixture is transferred to a first distillation column b) wherein most of the acetone is removed in a top stream and transferred back to the purification stage of the crude acetone while the mixture of organic compounds preferably is transferred to the second distillation column resulting in a bottom stream comprising an aqueous sodium hydroxide solution. In the preferred embodiment the bottom stream of the first distillation column contains beside the basic aqueous medium less than 2 wt %, preferably less than 1 wt % mesityl oxide and is recycled to the work-up process of the crude acetone stream in the Hock process.

The mixture of organic compounds transferred to the second distillation column is separated into a top stream containing acetone, a side stream containing organic substances with a boiling point lower than mesityl oxide and higher than acetone, like ketones and benzene, a further side stream containing mesityl oxide and a bottom stream containing cumene and optionally other compounds with a boiling point higher than mesityl oxide. The cumene containing bottom stream of the second distillation column is preferably recycled to the Hock process, optionally after preceding separation.

The recovered mesityl oxide is transferred back to the first distillation column at an entry point below the removing line of the organic compound mixture, preferably directly onto one of the reaction trays with which the distillation column is equipped. The temperature at the entry point is preferably 80-90° C.

The present invention shall be exemplified by means of a working example:

EXAMPLE 1

A waste stream was obtained from the acetone purification stage of the Hock process comprising 2 wt-% low boiling hydrocarbons, 11 wt-% acetone, 68 wt-% water, 10 wt-% mesityl oxide and 9 wt-% high boiling hydrocarbons and continuously fed to the middle section of a first distillation column as shown in FIG. 1. Based on 1000 parts by weight of waste stream, the waste stream was continuously separated into 150 parts by weight of a head product stream consisting essentially of acetone and containing only traces of low boiling hydrocarbons and into 713 parts by weight of a bottom stream consisting essentially of water and some high boiling hydrocarbons. A side stream was removed from the first distillation column and fed to a decanter, wherein the aqueous phase and the organic phase were separated. The aqueous phase was recycled to the first column and 279 parts by weight organic phase based on 1000 parts by weight of the waste stream, the organic phase comprising 7 wt-% low boiling hydrocarbons, 36 wt-% mesityl oxide, 25 wt-% acetone and 32 wt-% high boiling hydrocarbons, was continuously fed to a middle section of a second distillation column. The organic phase was continuously separated in 65 parts by weight of a head product stream consisting essentially of acetone, in 25 parts by weight of an upper side stream comprising 80 wt-% low boiling hydrocarbons and 20 wt-% acetone, 47 parts by weight of a bottom stream comprising high boiling hydrocarbons i.e. cumene and 142 parts by weight of a lower side stream comprising 70 wt-% mesityl oxide, 25 wt-% high boiling hydrocarbons and 5 wt-% acetone, all parts by weight being based on 1000 parts by weight of the initial waste stream. With upper side stream benzene was quantitatively removed from the waste stream. The lower side stream was continuously recycled to a lower portion of the first distillation column, where the mesityl oxide was converted to acetone as described above. As can be seen from this example valuable components like acetone, mesityl oxide converted to acetone and cumene can be economically recovered from a waste stream using the process of the present invention.

The present invention refers to a continuous process for recovering acetone from a waste stream from an acetone purification stage, said waste stream comprising mesityl oxide and optionally acetone by:
i) separating the waste stream in a separating device at least into one stream comprising mesityl oxide and optionally a further stream comprising acetone,
ii) concentrating mesityl oxide in the mesityl oxide containing stream and
iii) recycling the concentrated mesityl oxide stream to the separating device and bringing it into contact with a basic or acidic aqueous medium or with an acidic catalyst in the presence of water whereby mesityl oxide is at least partially hydrolyzed to acetone.

Preferably, concentrating of mesityl oxide is achieved by means of distillation.

More preferred, the concentrated mesityl oxide-containing stream contains at least 20, preferably 50 to 85% by weight of mesityl oxide.

According to a preferred embodiment of the present invention the separation device is a distillation column.

Preferably, the basic or acidic aqueous medium is separately fed to the separating device.

According to one embodiment the concentrated mesityl oxide containing stream is mixed with water and is contacted in the separation device with an acidic catalyst, preferably an immobilized heterogeneous catalyst.

Alternatively the basic or acidic aqueous medium is already present in the waste stream. Preferably, the concentration of the basic or acidic medium in the waste stream is $\geq 0.1\%$ by volume based on the complete volume of the waste stream.

According to a preferred embodiment of the present invention the waste stream comprises in addition one or more organic components having a boiling point higher than acetone, the basic or acidic aqueous medium is a basic medium and recovery of acetone is achieved by
a) continuously feeding said waste stream to a middle section of the first distillation column;
b) separating the waste stream in the first distillation column into
   b1) optionally a top stream comprising acetone;
   b2) a side stream comprising mesityl oxide, the organic components and optionally residual acetone,; and
   b3) a bottom stream comprising the basic aqueous medium;
c) continuously feeding side stream b2) to a middle section of the second distillation column;
d) separating the side stream b2) in the second distillation column into
   d1) a top stream comprising acetone;
   d2) a side stream comprising mesityl oxide; and
   d3) a bottom stream comprising organic components having a boiling point higher than mesityl oxide; and
e) continuously recycling side stream d2) to the first distillation column to an entry point that is below the removal point for side stream b2).

Preferably, the side stream b2) is continuously fed to a decanter, where the side stream is separated in an organic phase which is continuously fed to a middle section of the second distillation column and an aqueous phase which is at least partially recycled to the first distillation column.

Preferably, the first distillation column comprises reaction trays and the recycled mesityl oxide stream is directed onto one or more of the reaction trays. According to a preferred embodiment of the present invention the temperature at the entry point is 30 to 160° C., preferably 70 to 110° C.

Preferably, in the second distillation column a second side stream d4) comprising organic components having a boiling point lower than mesityl oxide is removed at a position upwards relative to the position of removal of side stream d2). Especially, side stream d4) comprises benzene.

According to a preferred embodiment of the present invention the waste stream results from the acetone purification of crude acetone obtained from the Hock process, whereby crude acetone is separated in a distillation column, wherein pure acetone is removed as top stream and the waste stream as bottom stream. Preferably any recovered acetone streams are combined and recycled to the acetone purification column.

Furthermore, in a preferred embodiment of the present invention refers to a process to manufacture phenol and acetone from cumene according to the Hock process by:
A) oxidizing cumene to form cumene hydroperoxide,
B) subjecting cumene hydroperoxide to acid-catalyzed cleavage obtaining a cleavage phase comprising phenol and acetone,
C) separating phenol and acetone,
D) purifying the crude acetone from step C) resulting in a pure acetone product stream and a waste stream; and
E) recovering acetone from the waste stream according to a process as defined above.

Preferably in the recovery step E) a process as defined above is used and wherein bottom stream d3) comprises cumene and is recycled to the Hock process and bottom stream b3) comprises the basic aqueous medium and less than 2 wt-%, preferably less than 1 wt-% mesityl oxide and is recycled to the work-up of acetone in the Hock process.

What is claimed is:

1. A method for recovering acetone from a waste stream from an acetone purification stage, wherein said waste stream comprises mesityl oxide, said method comprising:
   i) separating said waste stream in a separating device into at least a first stream comprising mesityl oxide;
   ii) concentrating said mesityl oxide, thereby producing concentrated mesityl oxide stream;
   iii) recycling said concentrated mesityl oxide stream into said separating device; and
   iv) bringing said concentrated mesityl oxide stream into contact with a basic aqueous medium, or with an acidic catalyst in the presence of water, whereby mesityl oxide is at least partially hydrolyzed to acetone,
wherein said waste stream further comprises one or more organic components having a boiling point higher than acetone, said method further comprising:
   a) continuously feeding said waste stream to a middle section of a first distillation column;
   b) separating said waste stream in said first distillation column into:
      b2) a side stream comprising mesityl oxide and said organic components, and
      b3) a bottom stream comprising said basic aqueous medium;
   c) continuously feeding said side stream b2) into a middle section of a second distillation column;
   d) separating said side stream b2) in said second distillation column into:
      d1) a top stream comprising acetone,
      d2) a side stream comprising mesityl oxide, and
      d3) a bottom stream comprising organic components having a boiling point higher than mesityl oxide; and
   e) continuously recycling side stream d2) to the first distillation column through an entry point that is below a removal point for said side stream b2).

2. The method of claim 1, wherein said waste stream further comprises acetone.

3. The method of claim 1, wherein said waste stream is further separated into at least a second stream comprising acetone.

4. The method of claim 1, wherein said concentrated mesityl oxide stream comprises at least 20% by weight of mesityl oxide.

5. The method of claim 4, wherein said concentrated mesityl oxide stream comprises at least between about 50% and about 85% by weight of mesityl oxide.

6. The method of claim 4, wherein said concentrated mesityl oxide stream is mixed with water and is contacted in said separating device with the acidic catalyst.

7. The method of claim 6, wherein said acidic catalyst is an immobilized heterogeneous catalyst.

8. The method of claim 1, wherein said basic aqueous medium is separately fed to the separating device.

9. The method of claim 1, wherein said basic aqueous medium is already present in the waste stream.

10. The method of claim 1, wherein said basic medium comprises at least about 0.1% by volume of said waste stream.

11. The method of claim 1, wherein said separating said waste stream in said first distillation column additionally yields: b1) a top stream comprising acetone.

12. The method of claim 1, wherein said side stream b2) further comprises residual acetone.

13. The method of claim 1, further comprising:
continuously feeding said side stream b2) to a decanter; and
separating said side stream b2) into:
   an organic phase, wherein said organic phase is continuously fed to a middle section of said second distillation column; and
   an aqueous phase, wherein said aqueous phase is at least partially recycled to said first distillation column.

14. The method of claim 1, wherein said first distillation column comprises reaction trays, said method further comprising directing said side stream d2) comprising mesityl oxide onto at least one of said reaction trays.

15. The method of claim 1, wherein a temperature at said entry point is between about 30° C. and about 160° C.

16. The method of claim 15, wherein said temperature at said entry point is between about 70° C. and about 110° C.

17. The method of claim 1, further comprising removing a second side stream d4) comprising organic components, said organic components having a boiling point lower than mesityl oxide, at a position upwards relative to a position of removal of said side stream d2).

18. The method of claim 17, wherein said second side stream d4) comprises benzene.

19. A method of manufacturing phenol and acetone from cumene according to a Hock process comprising:
   A) oxidizing said cumene to form cumene hydroperoxide;
   B) subjecting said cumene hydroperoxide to acid-catalyzed cleavage thereby obtaining a cleavage phase comprising phenol and acetone;
   C) separating phenol and crude acetone;
   D) purifying said crude acetone from step C), thereby obtaining a purified acetone product stream and a waste stream; and
   E) recovering acetone from said waste stream by the method of claim 1.

20. The method of claim 19, wherein said bottom stream d3) further comprises cumene and said bottom stream d3) is recycled to the Hock process; and wherein said bottom stream b3) comprises the basic aqueous medium and further comprises less than about 2 wt % mesityl oxide and said bottom stream b3) is recycled to the work-up of acetone in the Hock process.

21. The method of claim 20, wherein said bottom stream b3) comprises less than about 1 wt % mesityl oxide.

* * * * *